United States Patent
Ozaki et al.

(10) Patent No.: US 6,993,178 B2
(45) Date of Patent: Jan. 31, 2006

(54) LIFETIME EVALUATING SYSTEM OF MECHANICAL ELEMENT AND METHOD FOR THE SAME

(75) Inventors: Masashi Ozaki, Nagasaki-ken (JP); Nobuhiko Nishimura, Nagasaki-ken (JP); Nobuya Yoshimoto, Nagasaki-ken (JP); Shintaro Kumano, Hyogo-ken (JP); Naoto Kawase, Hyogo-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 698 days.

(21) Appl. No.: 10/115,978

(22) Filed: Apr. 5, 2002

(65) Prior Publication Data

US 2002/0146162 A1    Oct. 10, 2002

(30) Foreign Application Priority Data

Apr. 10, 2001 (JP) .............................. 2001-112015

(51) Int. Cl.
*G06K 9/00* (2006.01)

(52) U.S. Cl. ..................... 382/152; 702/34; 702/182; 700/175

(58) Field of Classification Search ............... 382/152; 702/34, 182–186; 700/175–176
See application file for complete search history.

(56) References Cited

U.S. PATENT DOCUMENTS

| | | | | |
|---|---|---|---|---|
| 4,845,763 A | * | 7/1989 | Bandyopadhyay et al. | . 382/152 |
| 4,875,170 A | * | 10/1989 | Sakurai et al. | ................. 702/34 |
| 5,291,419 A | * | 3/1994 | Satoh et al. | .................... 702/34 |
| 5,455,777 A | * | 10/1995 | Fujiyama et al. | ............. 702/34 |
| 5,571,966 A | * | 11/1996 | Tsuboi | ......................... 73/579 |
| 6,161,055 A | * | 12/2000 | Pryor | ......................... 700/175 |
| 6,249,599 B1 | * | 6/2001 | Kuroda | ....................... 382/152 |
| 6,567,752 B2 | * | 5/2003 | Cusumano et al. | ........... 702/34 |

* cited by examiner

*Primary Examiner*—Sanjiv Shah
*Assistant Examiner*—Aaron Carter
(74) *Attorney, Agent, or Firm*—Oblon, Spivak, McClelland, Maier & Neustadt, P.C.

(57) ABSTRACT

A lifetime evaluating system includes a digitalizing unit, an acquiring unit and a determining unit. The digitalizing unit digitizes an original metallographic image of a mechanical element to form a digital image. The acquiring unit acquires a plurality of labels from the digital image. Here, each of the plurality of labels is a set of pixels with a predetermined property. The determining unit classifies the plurality of labels into a class of voids and a class of non-voids based on evaluation data. A lifetime of the mechanical element is determined based on a number of labels in the void class and a size of each of the labels in the void class.

19 Claims, 18 Drawing Sheets

Fig. 3A  LOW LEVEL OF DEGRADATION
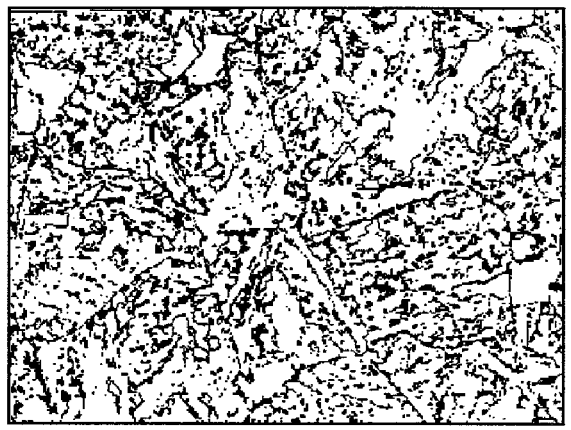
Fig. 3B  MIDDLE LEVEL OF DEGRADATION
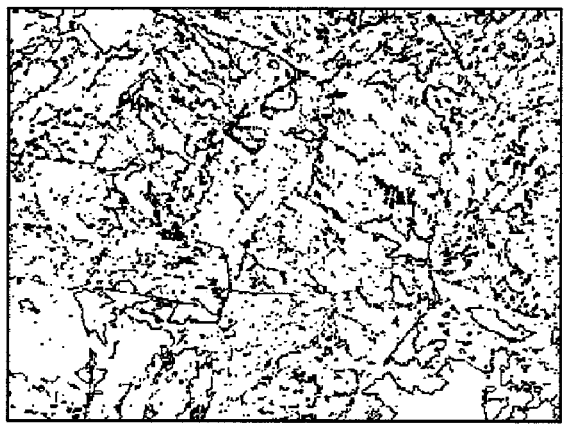
Fig. 3C  HIGH LEVEL OF DEGRADATION
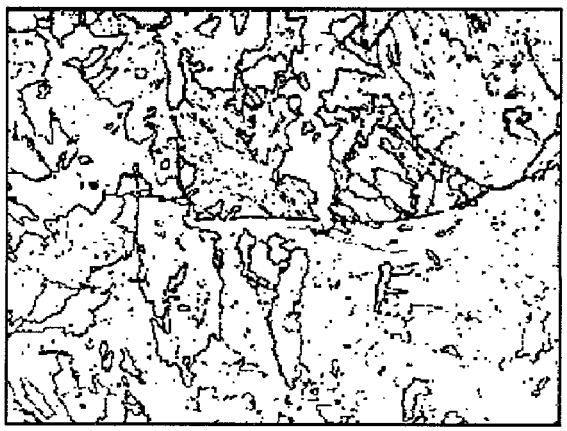

ORIGINAL IMAGE

BINARY IMAGE

CLEAR IMAGE

Fig. 9

| CLASS | LIFETIME CONSUMED PERCENTAGE (%) | STANDARD STRUCTURE I (OPTICAL MICROSCOPE) | STANDARD STRUCTURE II (SCANNING ELECTRON MICROSCOPE) | DETERMINATION CRITERIA | |
|---|---|---|---|---|---|
| $I_D$ | 0~50 | | | NO MECHANICAL DAME, OR GENERATION OF INDEPENDENT CREEP VOIDS | |
| $II_D$ | 50~75 | | | CONCATENATION OF CREEP VOIDS | CREEP VOIDS |
| $III_D$ | 75~80 | | | GENERATION OF MICRO CRACK | MICRO CRACK, CREEP VOIDS |
| $IV_D$ | 80~100 | | | GENERATION OF CRACK | CREEP VOIDS, CRACK, MICRO CRACK |

Fig. 11

INFLUENCE OF FEATURE QUANTITIES(*)

| | COARSE GRAIN REGION | SMALL GRAIN REGION | GRAIN MIXTURE REGION | WELDING REGION |
|---|---|---|---|---|
| AREA | 8% | 1% | 7% | 9% |
| LABEL LENGTH RATIO | 8% | 1% | 5% | 9% |
| BRIGHTNESS AVERAGE | 20% | 6% | 2% | 5% |
| BRIGHTNESS STANDARD DEVIATION | 3% | 7% | 6% | 11% |
| FILLING PERCENTAGE | 61% | 85% | 81% | 66% |
| TOTAL | 100% | 100% | 100% | 100% |

LIFETIME EVALUATING SYSTEM OF MECHANICAL ELEMENT AND METHOD FOR THE SAME

BACKGROUND OF THE INVENTION

1. Field of the Invention

The present invention relates to a lifetime evaluating system of material of a mechanical element and a method for the same.

2. Description of the Related Art

A machine such as a turbine of a thermal power generation plant has a machine element which operates at high temperature and in which the start and stop of the operation are frequently repeated. Such a mechanical element has a finite lifetime due to thermal fatigue and creep. Therefore, it is important to maintain the plant to allow the operation for a long term. Especially, the extension of durable years is important economically. For this purpose, a lifetime evaluation technique has been developed and requires high reliability.

A conventional lifetime evaluation is carried out through a metallographic check by an expert. As a non-destruction lifetime diagnosing method in which the metallographic change of metal material is evaluated, a metallographic comparison method is known. The metallographic comparison method has been developed as the lifetime evaluating method of brittle creep degradation in a welding portion of low alloy steel having a martensite structure. The metallographic comparison method is evaluated in high precision and is widely used as a periodical test method.

In the metallographic comparison method, as shown in FIG. 1, the metallographic structure of a test object portion of a mechanical element is copied as a replica 101. Also, a comparison table 109 is produced through the observation of creep cavities 103 by a scanning type electron microscope 102, the observation of a micro crack 105 and metallographic structure 106 by an optical microscope 104, and the observation of precipitation product 108 by an analysis electron microscope 107. In the comparison table 109, the damage state of the test object portion is classified into mechanical damage, optical microscopic metallographic damage, and precipitation product distribution damage based on damage factors. The optical microscopic metallographic damage and the precipitation product distribution damage contain metallographic changes such as the recovery of the martensite structure in the first half of the lifetime of the mechanical element and changes of a precipitation product distribution. The mechanical damage contains a mechanical change such as generation, combination and growth of creep voids and micro cracks in the second half of the lifetime. The degradation of the test object portion is determined based on a combination of three damage states. Each damage state is classified into classes. The classification is carried out based on the comparison of a sample with a standard specimen. The classes of the degradation correspond to the lifetime consumed percentages shown in the comparison table 109. The classification and comparison are carried out by the expert with material knowledge.

The classification with respect to the microscopic structure is exemplified as follows. A welding portion of CrMo steel is formed to have the martensite structure. When stress is applied to the martensite structure at high temperature, the structure is changed through the creep transformation. Such a change process is classified into degradation classes $I_M$, $II_M$, and $III_M$ by the expert, as shown in the column of the microscopic structure of the comparison table 109. The degradation class $I_M$ is equivalent to an unused state, in which a line structure called martensite lath can be clearly observed in a grain. The lifetime consumed percentage of the welding portion is 0–20%. The degradation class $II_M$ is a state, in which carbide is precipitated in the neighborhood of the boundary of martensite lath. The lifetime consumed percentage of the welding portion is 20–40%. The degradation class $III_M$ is a state, in which the martensite lath disappears, and carbide is precipitated in old austinite grain boundary. The lifetime consumed percentage of the welding portion is 40–100%. As mentioned above, the point to which the expert pays the most of attention in the classification of the degradation is the disappearance of the martensite laths. The line structure can be clearly confirmed in a non-damaged state, but becomes unclear gradually with the use time of the mechanical element. The expert determines the degradation based on a rate of martensite laths.

The classification with respect to the mechanical damage is exemplified as follows. The mechanical damage of the welding portion of CrMo steel is classified by the expert through quantification of creep voids generated as the creep damage progresses and micro cracks formed by combination of the creep voids. The mechanical damage is classified into four degradation classes $I_D$, $II_D$, $III_D$, and $IV_D$. The degradation class $I_D$ is a state, in which no creep void is generated or independent creep voids are generated. The lifetime consumed percentage is 0–50%. The degradation class $II_D$ is a state, in which the creep voids concatenate to each other, and the lifetime consumed percentage is 50–75%. The degradation class $III_D$ is a state, in which the creep voids concatenate along the whole boundary of the one crystal grain to generate a micro crack. The lifetime consumed percentage is 75–80%. The degradation class $IV_D$ is s state, in which the creep voids concatenate over the boundaries of the two or more crystal grains to generate the micro cracks. The lifetime consumed percentage is 80–100%.

This evaluating method strongly depends on the human ability of the expert and it is difficult to cope with the rapid increase of the lifetime evaluation object plants. Moreover, it is necessary to bring the sample or the data from the plant installation sites back to a laboratory, resulting in requirement of a lot of time.

SUMMARY OF THE INVENTION

Therefore, an object of the present invention is to provide a lifetime evaluating system and a method for the same, in which a remaining lifetime of a mechanical element can be evaluated in short time.

Another object of the present invention is to provide a lifetime evaluating system and a method for the same, in which the evaluation of the remaining lifetime is as precise as evaluation by an expert.

Still another object of the present invention is to provide a lifetime evaluating system and a method for the same, in which the evaluation can be automated.

In an aspect of the present invention, a lifetime evaluating system includes a digitalizing unit, an acquiring unit and a determining unit. The digitalizing unit digitizes an original metallographic image of a mechanical element to form a digital image. The acquiring unit acquires a plurality of labels from the digital image. Here, each of the plurality of labels is a set of pixels with a predetermined property. The determining unit classifies the plurality of labels into a class of voids and a class of non-voids based on evaluation data.

A lifetime of the mechanical element is determined based on a number of labels in the void class and a size of each of the labels in the void class.

The lifetime evaluating system may further include a calculating unit which calculates the evaluation data from teacher labels.

The determining unit determines the lifetime of the mechanical element based on the number of labels in the void class and the size of each of the labels in the void class.

Also, the digitalization may be a binary coding, and the predetermined property may be a brightness of the pixel.

Also, the evaluation data includes a filling percentage $r_C$ defined in the following equation, $$r_C = N_A/N_R$$

wherein $N_A$ is a number of pixels in each of the plurality of labels, and $N_R$ is a number of pixels around the label.

Also, the evaluation data includes an area percentage $r_{HAZ}$ defined by the following equation, $$r_{HAZ} = N_M/N_T$$

where $N_M$ is a total number of pixels in the label, and $N_T$ is a total number of pixels of the digital image.

Also, the evaluation data may include a coefficient vector and a threshold value. Also, the determining unit may generate a feature vector from each of the plurality of labels, and classifies the plurality of labels into the void class and the non-void class based on the feature vectors, the coefficient vector and the threshold value.

In this case, the determining unit may calculate an inner product of each of the feature vectors and the coefficient vector, and classifies the inner products based on the threshold value. Also, the feature vector may have geometrical feature quantities and optical feature quantities.

In this case, one of the geometrical feature quantities may be a filling percentage $r_C$, and one of the optical feature quantities may be a normalized brightness average, the filling percentage is shown by the following equation, $$r_C = N_A/N_R$$

wherein $N_A$ is a number of pixels in each of the plurality of labels, and $N_R$ is a number of pixels around the label, and the normalized brightness $S_A$ is shown by n $$S_A = (B_L - B_A)/H_A$$

where $B_L$ is an average brightness of one label, $B_A$ is an average brightness of a whole of the digital image, and $H_A$ is a brightness standard deviation of a whole of the digital image.

Also, one of the optical feature quantities may be a normalized brightness average $S_H$ defined by the following equation, $$S_H = H_L/H_A$$

where $H_L$ is the brightness standard deviation of one label, and $H_A$ is a brightness standard deviation of a whole of the digital image.

Also, one of the geometrical feature quantities may be an aspect ratio $r_A$ defined by the following equation, $$r_A = A_L/A_S$$

where $A_L$ is a long axis length of one label and $A_S$ is a short axis length.

Also, one of the geometrical feature quantities may be an area percentage $r_{HAZ}$ defined by the following equation, $$r_{HAZ} = N_M/N_T$$

where $N_M$ is a total number of pixels in the label, and $N_T$ is a total number of pixels of the digital image.

here, in a separation $\theta$ between the void class and the non-void class, a denominator of the separation $\theta$ is a summation of an intra-variance of the void class and that of the non-void class, and a numerator of the separation $\theta$ is an inter-class variance, and the coefficient vector is calculated such that the separation $\theta$ is maximized.

In this case, $$\theta = (I^T d)^2 [\{I^T(S_{C1}+S_{C2})I\}(n_{C1}+n_{C2}-2)]$$

where $n_{C1}$ is the number of labels in the void class, $n_{C2}$ is the number of labels in the non-void class, I is a matrix of the coefficient vector, T of an upper right subscript means transposition of a matrix, $S_{C1}$ is a matrix having as one element, a summation of squares of difference of one of feature quantities of each of the feature vectors from an average corresponding to the one feature quantity in the void class, $S_{C2}$ is a matrix having as one element, a summation of squares of difference of one of feature quantities of each of the feature vectors from an average corresponding to the one feature quantity in the non-void class, and d is a matrix of difference of a feature average vector in the void class and a feature average vector in the non-void class.

In another aspect of the present invention, a lifetime evaluating method is achieved by (a) digitalizing an original metallographic image of a mechanical element to form a digital image; by (b) acquiring a plurality of labels from the digital image, wherein each of the plurality of labels is a set of pixels with a predetermined property; by (c) classifying the plurality of labels into a class of voids and a class of non-voids based on evaluation data; and by (d) determining the lifetime of the mechanical element based on the number of labels in the void class and the size of each of the labels in the void class.

The lifetime evaluating method may further include (e) calculating the evaluation data from teacher labels.

When the evaluation data includes a coefficient vector and a threshold value, the (c) classifying step may be achieved by generating a feature vector from each of the plurality of labels, the feature vector has a plurality of feature quantities as elements; and by classifying the plurality of labels into the void class and the non-void class based on the feature vectors, the coefficient vector and the threshold value.

The (c) classifying step may be achieved by calculating an inner product of each of said feature vectors and said coefficient vector; and by classifying the detection labels based on the inner products and said threshold value.

Also, one of the plurality of feature quantities may be a filling percentage $r_C$ defined in the following equation, $$r_C = N_A/N_R$$

wherein $N_A$ is a number of pixels in each of the plurality of labels, and $N_R$ is a number of pixels around the label.

Also, one of the plurality of feature quantities may be an area percentage $r_{HAZ}$ defined by the following equation, $$r_{HAZ} = N_M/N_T$$

where $N_M$ is a total number of pixels in the label, and $N_T$ is a total number of pixels of the digital image.

Also, one of the geometrical feature quantities may be a filling percentage $r_C$, and one of the optical feature quantities is a normalized brightness average, the filling percentage is shown by the following equation, $$r_C = N_A/N_R$$

wherein $N_A$ is a number of pixels in each of the plurality of labels, and $N_R$ is a number of pixels around the label, and the normalized brightness $S_A$ is shown by n $$S_A = (B_L - B_A)/H_A$$

where $B_L$ is an average brightness of one label, $B_A$ is an average brightness of a whole of the digital image, and $H_A$ is a brightness standard deviation of a whole of the digital image.

Also, one of the optical feature quantities may be a normalized brightness average $S_H$ defined by the following equation, $$S_H = H_L/H_A$$

where $H_L$ is the brightness standard deviation of one label, and $H_A$ is a brightness standard deviation of a whole of the digital image.

Also, one of the plurality of feature quantities may be an aspect ratio $r_A$ defined by the following equation, $$r_A = A_L/A_S$$

where $A_L$ is a long axis length of one label and $A_S$ is a short axis length.

Also, in a separation θ between the void class and the non-void class, a denominator of the separation θ is a summation of an intra-variance of the void class and that of the non-void class, and a numerator of the separation θ is an inter-class variance, and the coefficient vector is calculated such that the separation θ is maximized.

In still another aspect of the present invention, a program for executing by a computer system, any one of the lifetime evaluating methods mentioned above.

BRIEF DESCRIPTION OF THE DRAWINGS

FIGS. 3A to 3C are diagrams showing degradation levels of material;

FIG. 9 is a determination table showing a relation between creep voids and micro cracks and remaining lifetime;

FIG. 11 is a table showing influence of the feature quantity;

DESCRIPTION OF THE PREFERRED EMBODIMENTS

Hereinafter, a lifetime evaluating system of the present invention will be described in detail with reference to the attached drawings.

Figure 1:
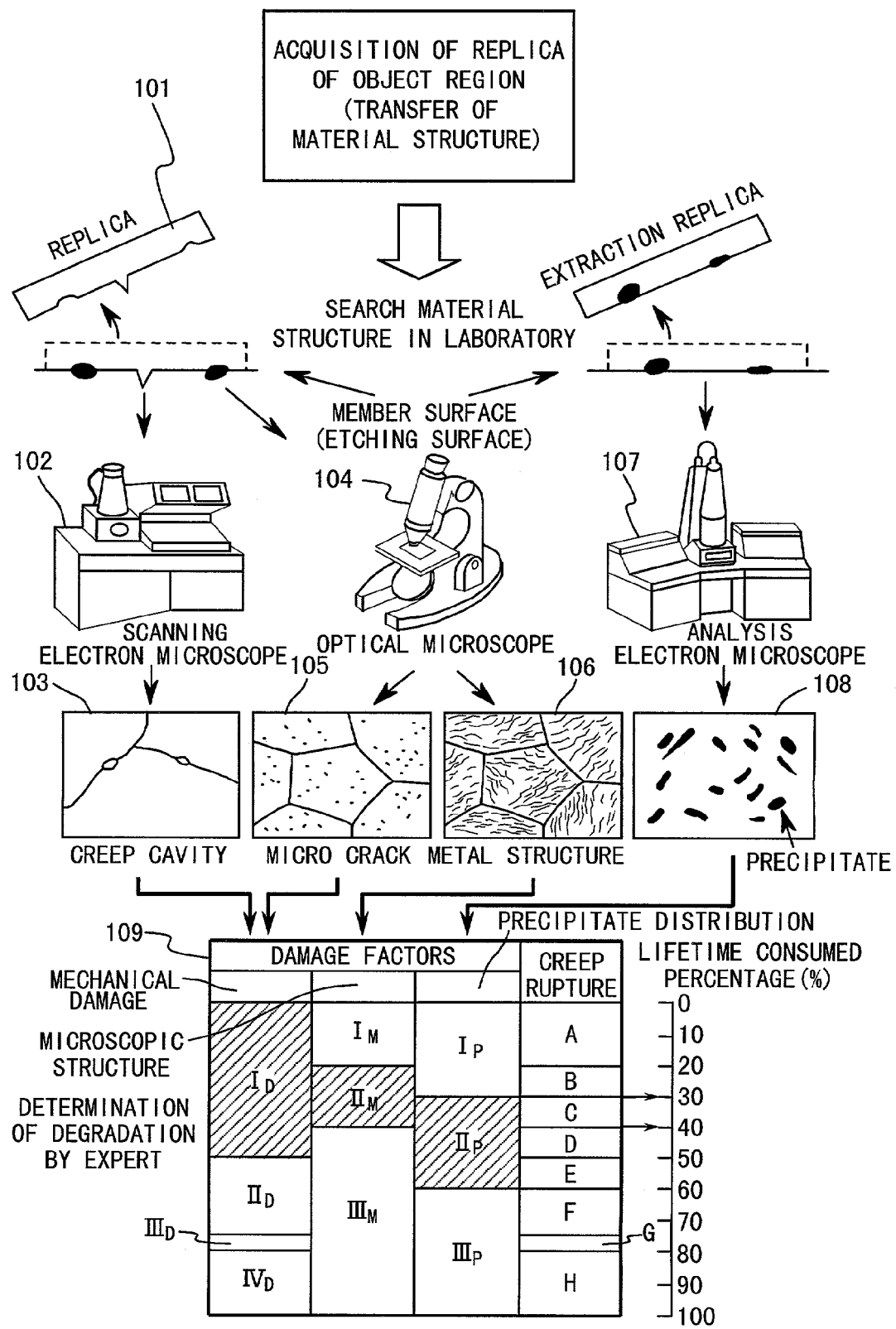
FIG. 1 is a diagram showing a conventional material lifetime evaluating method.
Figure 2:
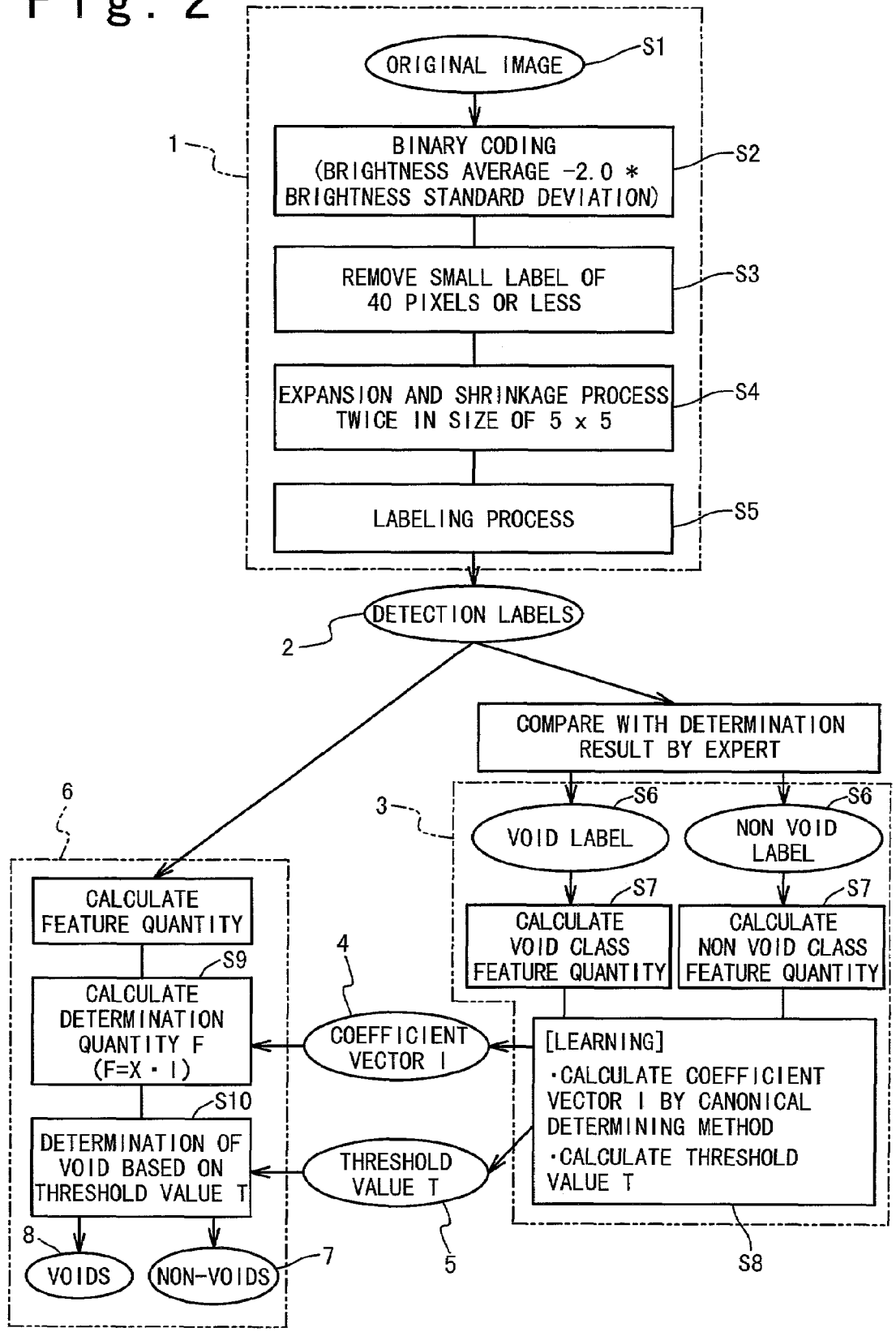
FIG. 2 is a block diagram showing a lifetime evaluating system according to an embodiment of the present invention.

FIG. 2 shows the lifetime evaluating system according to the first embodiment of the present invention. Referring to FIG. 2, the lifetime evaluating system in the first embodiment is comprised of a data generating unit 1 which carries out a data acquisition process, a calculating unit 3 which carries a learning process to output a coefficient vector and a threshold value, and a void determining unit 6 which carries out a void determining process.

As shown in FIG. 2, the data generating unit 1 generates and outputs detection labels 2 as basic data for void determination based on an original metallographic image. The detection labels 2 are supplied to the void calculating unit 3 as teacher data or to the void determining unit 6 as test data. The void calculating unit 3 calculates a plurality of feature quantities of a void class. The void calculating unit 3 calculates a coefficient vector I and a threshold value T based on the plurality of feature quantities by using a canonical determining method, and outputs the coefficient vector I 4 and the threshold value T 5 to the void determining unit 6. The void determining unit 6 distinguishes voids 8 from non-voids 7 other than voids, and determines a lifetime of the mechanical element.

Figure 4A:
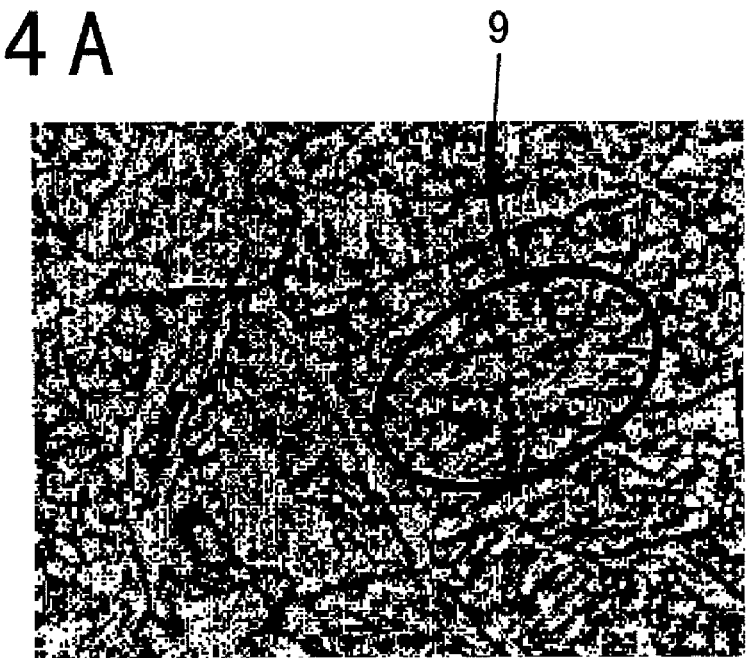
FIGS. 4A and 4B are diagrams showing two state of martensite lath.
Figure 4B:
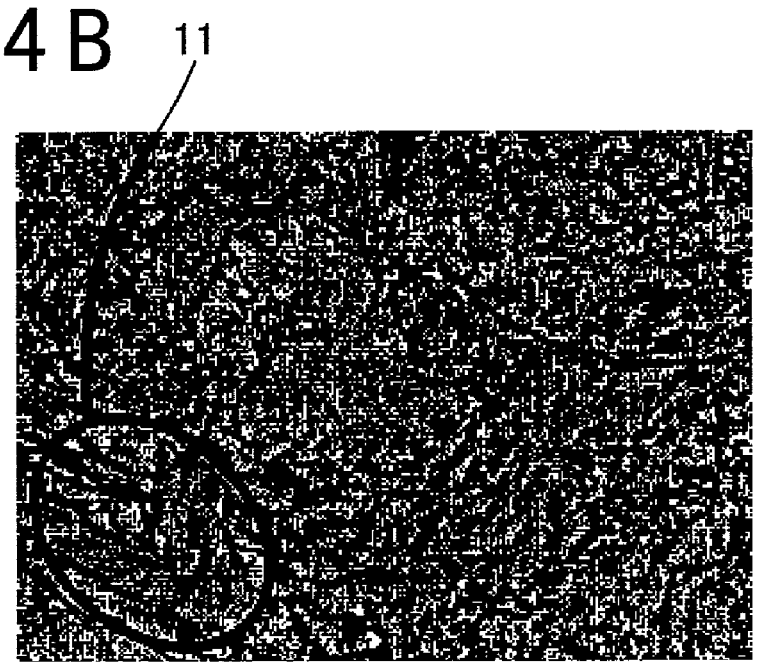

The metallographic comparison method has a process of quantitative representation of martensite laths which are a line structure in a grain appearing on the metallographic structure surface, as mentioned above. FIGS. 3A to 3C show wide range photographs of the martensite laths in a coarse grain region influenced by welding heat, and respectively show three degradation classes of a low level of degradation, a middle level of degradation and a high level of degradation. FIGS. 4A and 4B show microphotographs of the martensite laths of the coarse grain region. FIG. 4A shows martensite laths 9 in the low level of degradation, and FIG. 4B shows martensite laths 11 in the middle level of degradation which is now growing. FIGS. 4A and 4B shows that the martensite laths become illegible and disappear if the degradation proceeds.

The relation of the disappearance of the martensite laths and the structure degradation provides important basis data for the remaining lifetime evaluation. Non-degraded lath regions are extracted from an original image to provide the basis data to distinguish degraded lath regions.

FIG. 2 shows a process of evaluating a material lifetime according to the present invention with the configuration of the above computer unit which executes a program for the process. An original metallographic image 12 is obtained by a microscope at a step S1.

Figure 5:
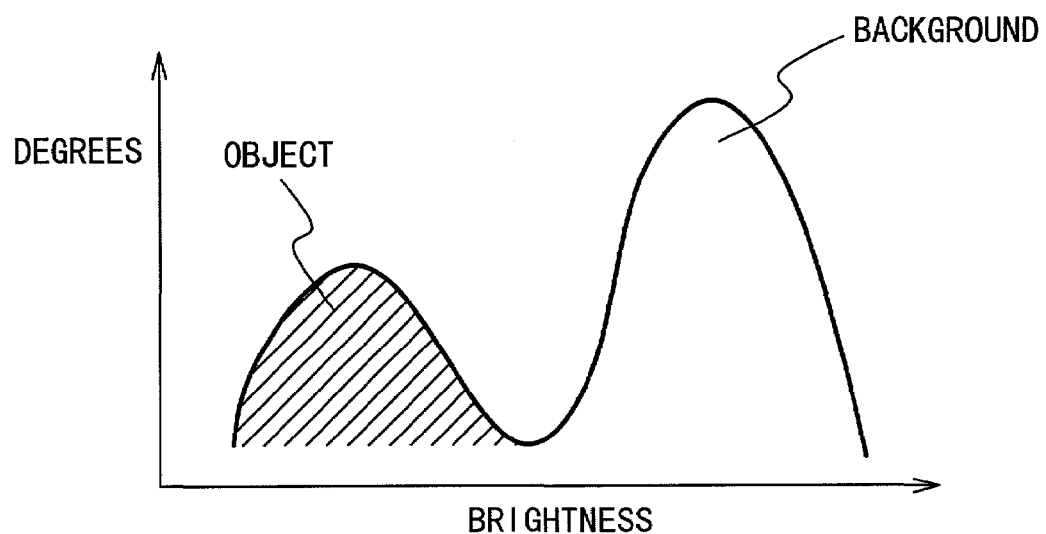
FIG. 5 is a diagram showing a binary coding process.

At step S2, a binary coding process is carried out with respect to brightness. The original image 12 is produced as a set of pixels. The original image 12 which has been subjected to the binary coding process is divided into an object region and a background region. The object region is a set of pixels with the brightness of 1, and the background region is a set of pixels with the brightness of 0. The crystal grain boundary is extracted as the non-degraded lath region, and the extraction of the crystal grain boundary never has an influence on the remaining lifetime evaluation. The bright images in the object region are allocated with labels. Here, in the binary coding process, a pixel is distinguished based on whether or not the pixel has brightness higher than a threshold value. The threshold value is defined as (brightness average−2.0×brightness standard deviation). However, the threshold value is not limited to such a definition, and another threshold value may be defined. FIG. 5 shows a threshold value determination method for the binary coding process using a canonical determining method. The brightness, based on which the pixels can be classified into an object region and a background region, is selected as the threshold value.

Figure 7A:
FIGS. 7A to 7C are photographs showing 3 images of a lath.
Figure 7B:
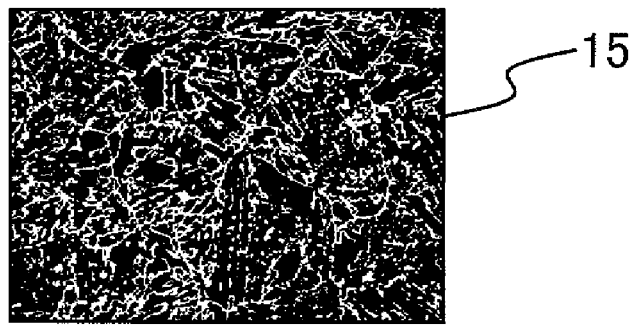
Figure 7C:
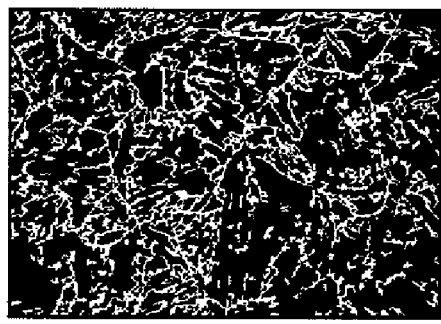

At a step S3, small images in the object region are removed. A reference value for the removal is 40 pixels. FIGS. 7A to 7C show the original metallographic image 12, the binary coded image 15 and a clear image 16 after the removal of the small images, respectively.

The clear images extracted in this way are corrected using an expansion and shrinkage process at a step S4. The expansion and shrinkage process is a mathematical process, in which the binary value of pixels around one label is changed to the binary value of the label to produce a new larger label and then the binary value of the pixels around the new larger label is inverted to the original binary value. For example, when there are two labels of nine pixels of 3×3 apart from each other by two pixels, the two labels of nine pixels are concatenated to produce a single larger label of 5×10 through the expansion process. Then, peripheral pixels are removed through the shrinkage process to produce a single smaller label of 3×8. The pixel whose binary value is changed through the expansion and shrinkage process is estimated to be a pixel generated based on noise. The clear images are corrected through the inversion of the binary value. The correction may be achieved through the two cycles of the expansion and shrinkage process. The above image correction is carried out in the size of 5×5 pixels. After the image correction, new labels are allocated to the labels after the expansion and shrinkage process at a step S5.

The labels of the clear images as detection labels 2 are outputted from the data generating unit 1 to the void calculating unit 3 as teacher labels or to the void determining unit 6 as test labels.

At a step S6, the expert classifies the detection labels as the teacher data into a void class and a non-void class using the conventional lifetime evaluating method. At a step S7, the calculating unit 3 calculates feature quantities of the labels in the void class and feature quantities of the labels in the non-void class.

Then, a step S8, the calculating unit 3 calculates a coefficient vector I 4 having the calculated feature quantities as elements and a threshold value T 5 through a learning process to many samples of detection labels. The calculating unit 3 outputs the coefficient vector I 4 and the threshold value T 5 to the void determining unit 6.

Next, the feature quantities will be described.

Figure 10:
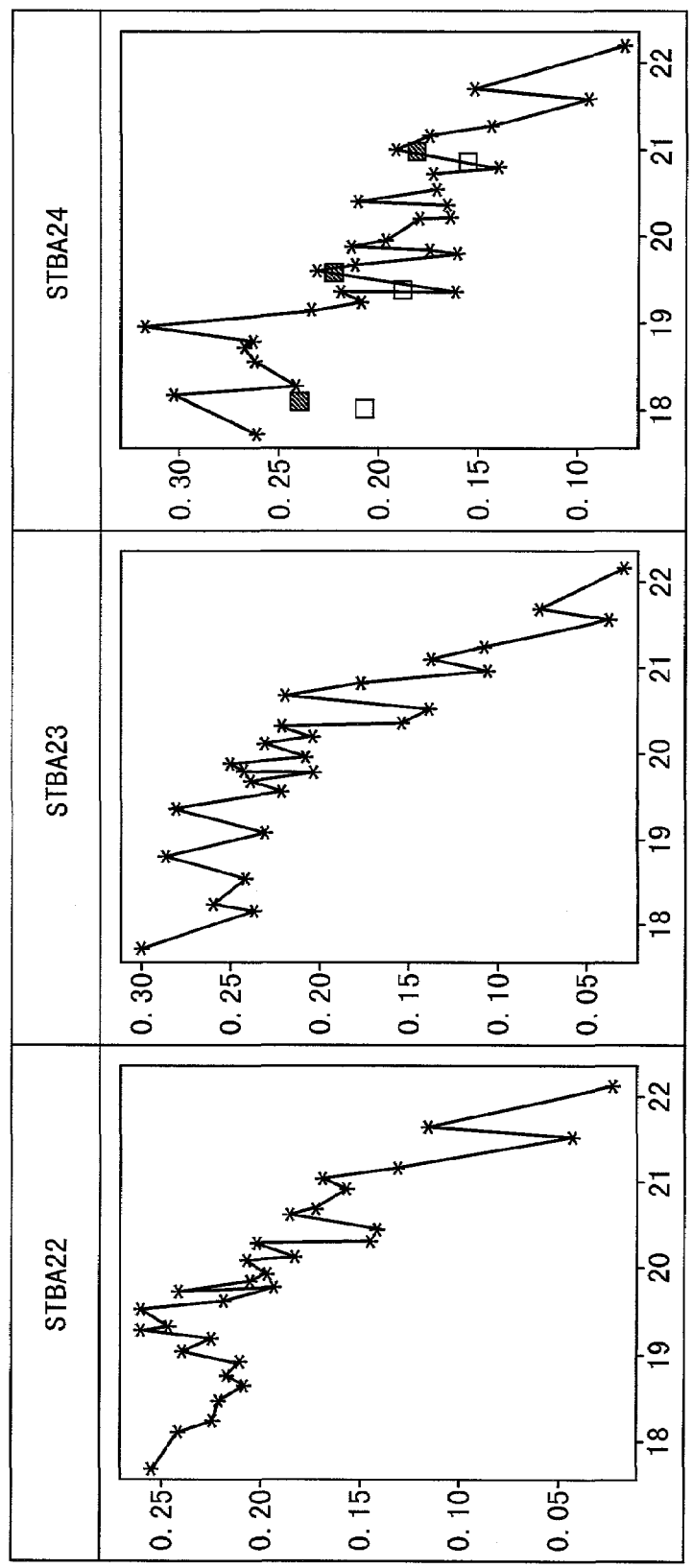
FIG. 10 is a graph showing correlation between feature quantity and idiomatic parameter.

One feature quantity of the label is an area percentage $R_{HAZ}$ in the following definition:

$$R_{HAZ} = N_M/N_r$$

where $N_M$ is the number of pixels in the lath image, and $N_r$ is a total numbers of pixels. FIG. 10 shows the coincidence of the area percentage $R_{HAZ}$ and Larson-Miller parameter LMP which is a usual factor of the determination of the degradation. The Larson-Miller parameter LMP is defined as the following equation.

$$LMP = T(C + \log t)/1000$$

where T is an absolute temperature (K), C is a constant value (20 is usually adopted), and t is a heating time (hr).

As the materials used for comparison, three kinds of materials such as STBA22, STBA23 and STBA24 are selected which are often used in a portion of a heat transfer pipe of a thermal power generation plant where a possibility of the damage occurrence is high. As samples, butt joints are produced by a matting arc welding method, and are subjected to heat treatment in the following condition. The welding heat-treatment condition is to maintain at the temperature of 715° C. for 15 minutes and to cool in air naturally.

The horizontal axis of FIG. 10 shows LMP and the vertical axis shows the above-mentioned area percentage $R_{HAZ}$. The correlation of LMP and the area percentage $R_{HAZ}$ is 90%. The examinations carried out changing the heating treatment condition variously show high correlations. The other feature quantities show high correlation with LMP, too.

Figure 8:
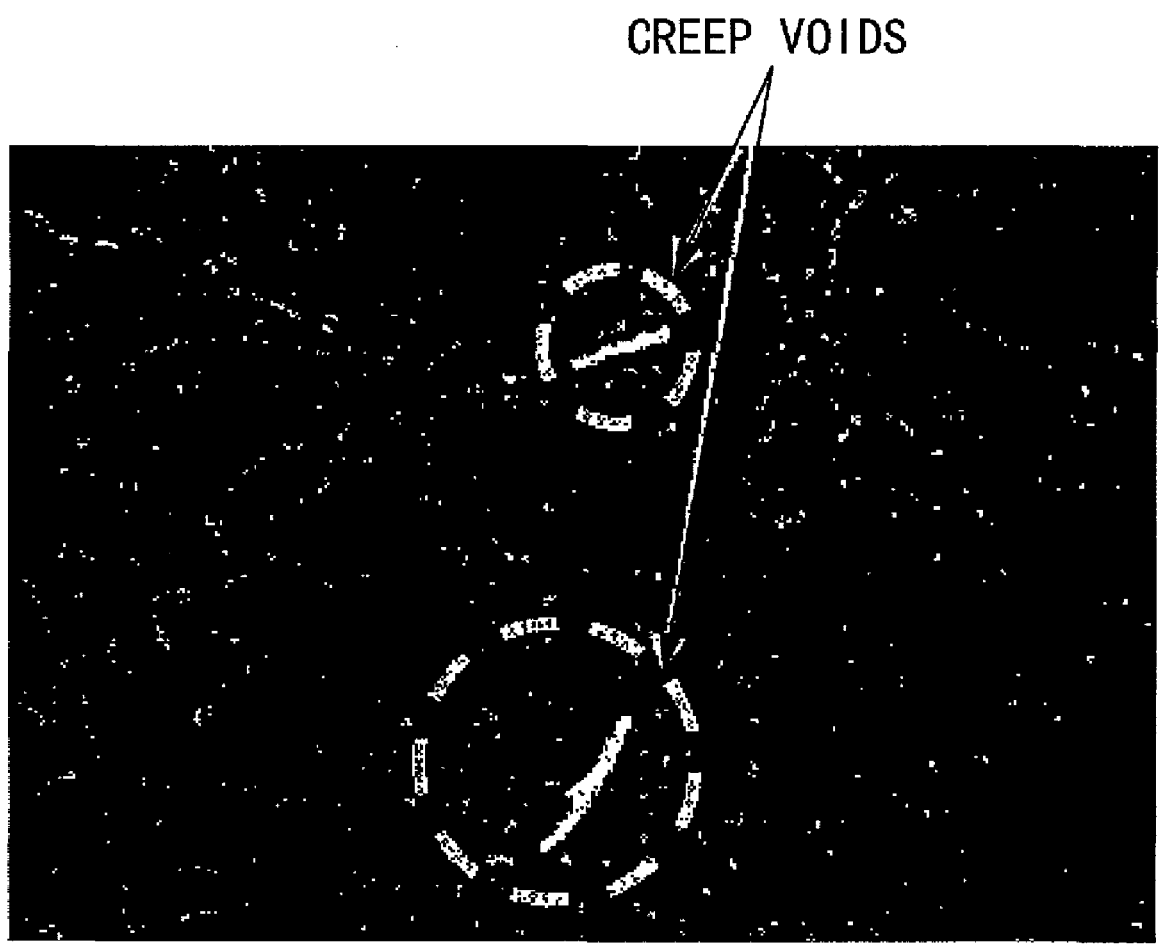
FIG. 8 is a photograph showing creep voids.

FIG. 8 shows a microscope image of a creep void in a dotted line circle. The void is more circular, compared with the grain boundary, and the grain boundary having the line structure is low in the circular degree, compared with the void. The feature quantity of such a circle is an important factor to distinguish the void from the non-void. The circle feature is expressed as a circular feature quantity or a filling percentage. The circular feature quantity $r_C$ is defined by the following equation for each label:

$$r_C = N_A/N_R$$

where $N_A$ is the number of pixels in the label, and $N_R$ is the number of pixels in a predetermined circular neighborhood region of the label. This value $r_C$ has the smallest value in case of a full circle.

The degradation never appears as only one feature quantity. The circular feature quantity is one important factor to indicate the degradation. However, if there are more feature quantities, the degradation can be determined in higher precision. The following four effective feature quantities exist. As the four effective feature quantities, there are the above-mentioned area percentage $R_{HAZ}$, an aspect ratio $r_A$, a normalized brightness average $S_A$, and a normalized brightness standard deviation $S_H$.

The aspect ratio $r_A$ is expressed by the following equation, $$r_A = A_L/A_S$$

where $A_L$ is a label longer axis length, and $A_S$ is a label shorter axis length (the shorter axis is orthogonal to the longer axis).

The normalized brightness average SA is expressed by the following equation, $$SA = (B_L - B_A)/H_A$$

where $B_L$ is an average brightness of the label, $B_A$ is an average brightness of the whole image, and $H_A$ is the brightness standard deviation of the whole image.

The normalized brightness standard deviation $S_H$ is expressed by the following equation, $$S_H = H_L/H_A$$

where $H_L$ is a brightness standard deviation of the label, and $H_A$ is a brightness standard deviation of the whole image.

At the step S8, weighting coefficients of the five feature quantities for the degradation determination are calculated. If the number of feature quantities is 5, the number of weighting coefficients is 5. In the step S8, the weighting coefficients of the weighting coefficient vector I are calculated through the learning process using the feature quantities in the void class and the feature quantities in the non-void class. The weighting coefficient vector I is shown as a side matrix (I1, I2, I3, I4, I5) or a transposed matrix of this matrix. Also, the threshold value T is calculated to separate the void class and the non-void class. The calculated coefficient vector I and the threshold value T are supplied to the void determining unit 6.

The weighting coefficient vector I and the threshold value T are calculated such that θ of the following equation (1) is maximized.

$$\theta = qZ^2 / \{V_z(n_{C1} + n_{C2} - 2)\} \quad (1)$$
$$= (I^T d)^2 / [\{I^T\{S_{C1} + S_{C2}\}I\}(n_{C1} + n_{C2} - 2)]$$

where the upper right subscript T shows the transposition of the matrix, and qZ is an inter-class variance and is shown by the following equation (2).

$$qZ^2 = (I^T \bar{x}_{C1} - I^T \bar{x}_{C2})^2 \quad (2)$$
$$= \{I^T(\bar{x}_{C1} - \bar{x}_{C2})\}^2$$
$$= (I^T d)^2$$

where $C_1$ and $C_2$ show class 1 (corresponding to the void class) and class 2 (corresponding to the non-void class), respectively, and the symbol "–" as the upper right subscript shows an average.

$V_Z$ of the equation (1) has the summation of squares in each of the classes as an element and is shown as the following equation (3).

$$V_Z = V_{Z,C1} + V_{Z,C2} \quad (3)$$
$$= I^T S_{C1} I + I^T S_{C2} I$$
$$= I^T (S_{C1} + S_{C2}) I$$

$V_{Z,C}$ represents each of the summations of squares $V_{Z,C1}$ and $V_{Z,C2}$ in the classes and is shown as the following equation (4).

$$V_{Z,C} = \sum_{k \in C} (I^T x_k - I^T \bar{x}_C)^2 \quad (4)$$
$$= \sum_{k \in C} \left\{ \left( \sum_{i=1}^{P} \sum_{j=1}^{P} I_i I_j (x_{ki} - \bar{x}_i^-)(x_{kj} - \bar{x}_j^-) \right) \right\}$$
$$= \left( \sum_{i=1}^{P} \sum_{j=1}^{P} I_i I_j \{ \sum k \in C (x_{ki} - \bar{x}_i^-)(x_{kj} - \bar{x}_j^-) \} \right)$$
$$= I^T S_{CI}$$
$$= \text{each term of the right side in the equation (3)}$$

where $S_C$ is a sum of product matrix of summations of squares of deviations of feature quantity vectors x of the C class and is shown as the following equation (5). The lower right subscript $k \in C$ of $\Sigma_{k \in C}$ means summation with respect to k belonging to a set C. The upper right subscript and the lower right subscript of $\Sigma_{j=1}^P$ mean a summation from j=1 to j=p. Here, p is the number of feature quantities and is 5 in this case. The variable k shows the number of void labels.

$$S_C = \{\Sigma_{k \in C}(x_k - \bar{x}_C)(x_k - \bar{x}_C)^T\} \quad (5)$$

nC ($n_{C1}$, $n_{C2}$) of the equation (1) is the number of data, i.e., the number of voids or labels in the class C ($C_1$, $C_2$). The vector d of the equation (1) is the difference of the feature quantity average vectors for two classes and is shown by the following equation (6).

$$d = \bar{x}_{C1} - \bar{x}_{C2} \quad (6)$$

The following equation is satisfied between $S_C$ and I such that θ of the equation (1) takes maximum.

$$(S_{C1} + S_{C2})I = Cd \quad (7)$$

The weighting coefficient vector I is calculated from this equation.

$$I = C(S_{C1} + S_{C2})^{-1} d \quad (8)$$

where C in the right side of the equation (7) is a properly defined constant.

The void calculating unit 3 calculates the feature quantity threshold value T for each feature quantity to distinguish the voids from the non-voids clearly at the step 8. The calculation of the threshold value T is properly adopted from a mathematical processing methods, and especially, the canonical determining method can be adopted. The weighting coefficient vector I 4 and the threshold value T 5 are outputted from the void calculating unit 3 to the void determining unit 6.

More specifically, the teacher labels are classified two classes C1 and C2 as follows in more details. The object original metallographic image 12 is subjected to the above-mentioned labeling process at the step S5 by the data generating unit 1 and a group of the detection labels are outputted. The object original metallographic image 12 is the label group which has been confirmed and prepared by the expert and which is called a teacher label. The teacher label is subjected to the above-mentioned binary coding process at the step S2, the small label removing process at the step S3, the expansion and shrinkage process at the step S4 and the labeling process at the step S5. The labels are classified into following three groups based on the detection labels and the teacher label. Three labels are defined as follows.

A right label: A partial set where the teacher label and the determination object label overlap each other.

An error detection label: A set where the teacher label and the determination object label do not overlap each other.

A miss label: A partial set of the teacher label where the teacher label and the determination object label do not overlap each other.

The above-mentioned class C1 is a total set of the right label and the error detection label and is called a void class. The above-mentioned class C2 is the miss label and is called the non-void class.

FIG. 11 shows the calculation result about 4 areas as the evaluation object parts of the sample. The left column shows five feature quantity components x. The other columns show the values corresponding to coefficient vector I as {absolute value of (the weighting coefficients×standard deviation) of each feature quantity}/{a summation of the absolute values of (the weighting coefficients×standard deviation) of the feature quantity}. The corresponding values are calculated for four areas (coarse grain region, small grain region, a grain mixture region, and a welding region). As shown in the table of FIG. 11, the above-mentioned circular feature quantity (the filling percentage) as the influence degree is large in the whole areas.

Figure 12:
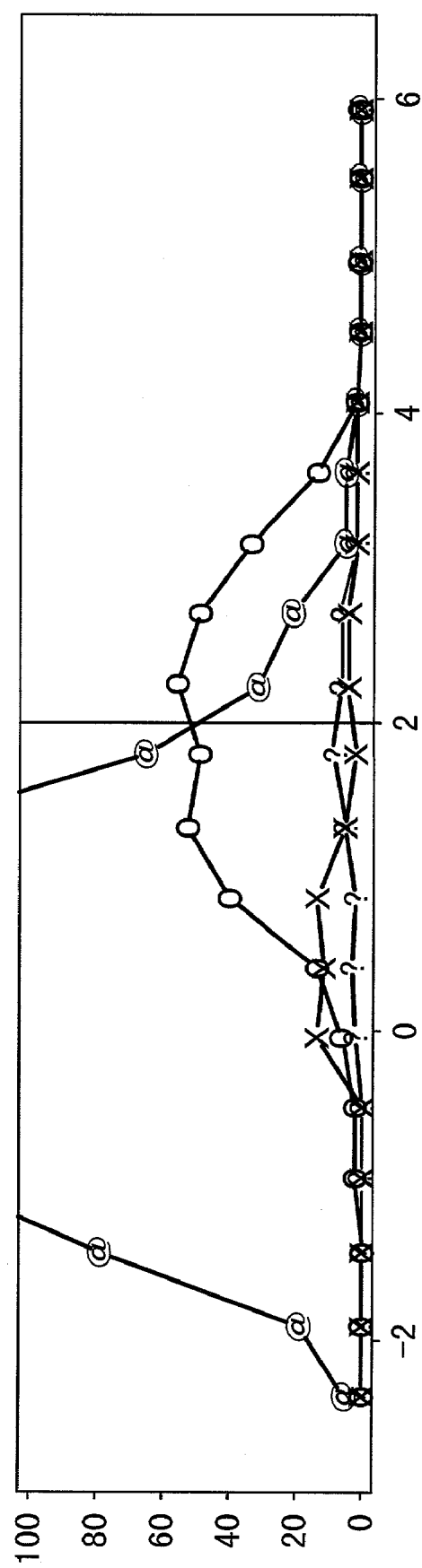
FIG. 12 is a graph showing angular variance of the evaluation factor.
Figure 13:
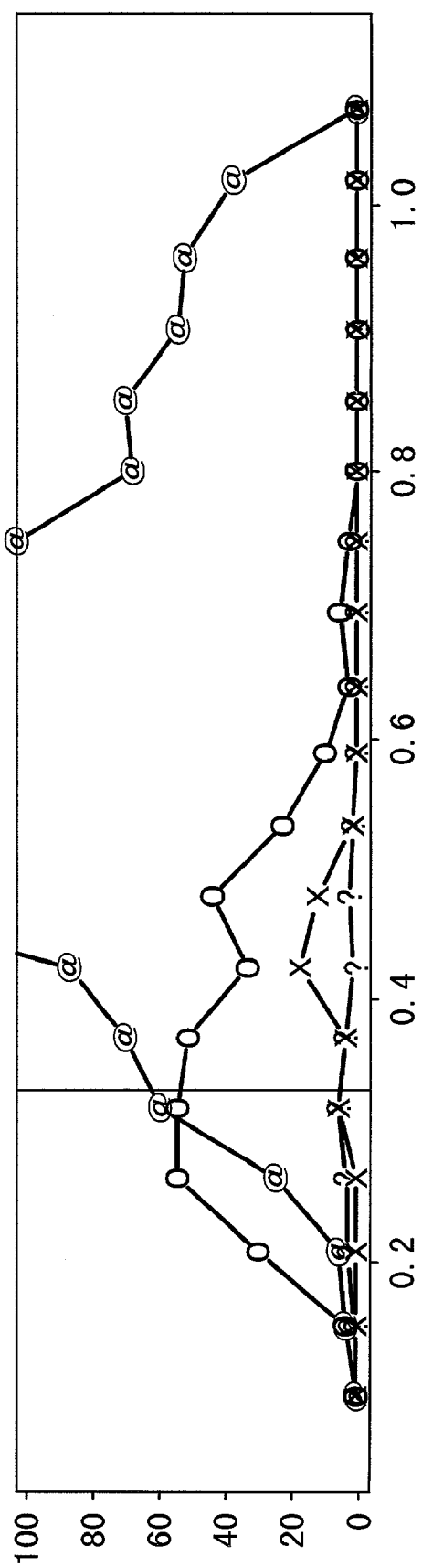
FIG. 13 is a graph shows angular variance of the feature quantity.
Figure 14:
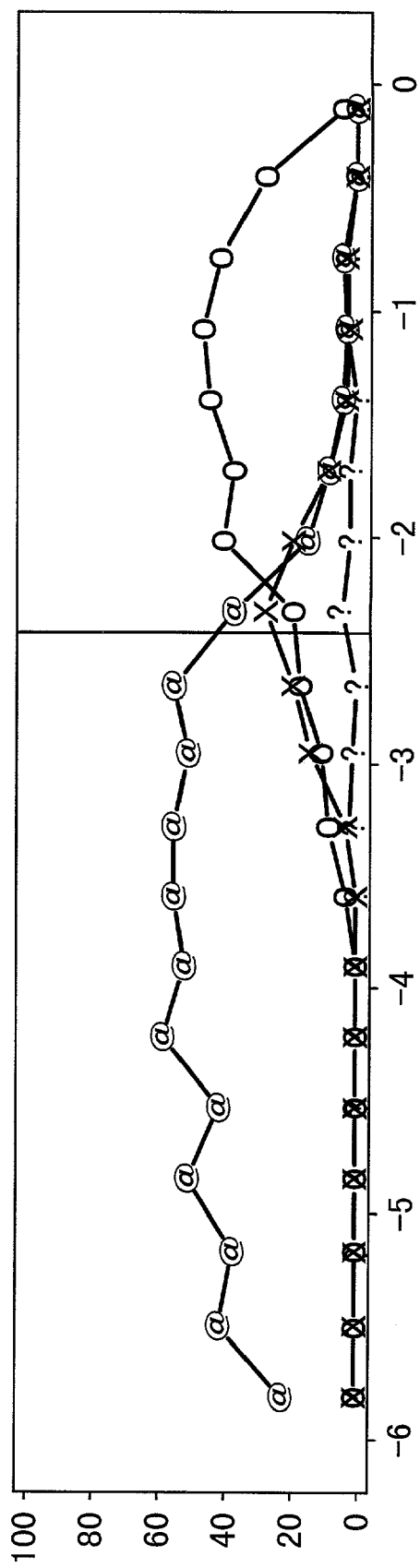
FIG. 14 is a graph showing other angular variance of the evaluation factor.
Figure 15:
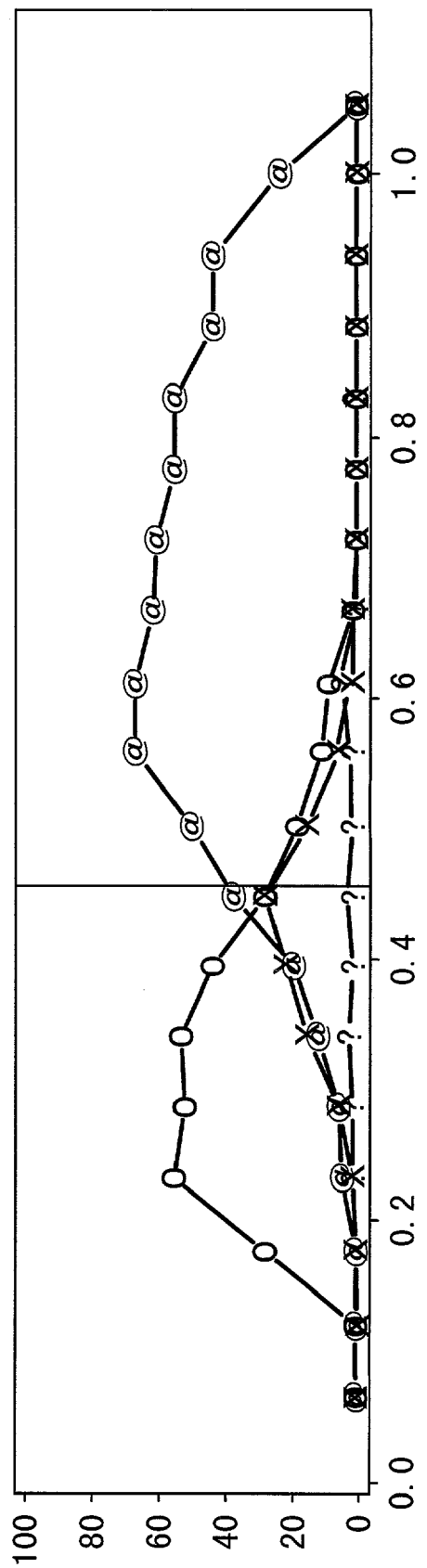
FIG. 15 is a graph showing other angular variance of the feature quantity.
Figure 16:
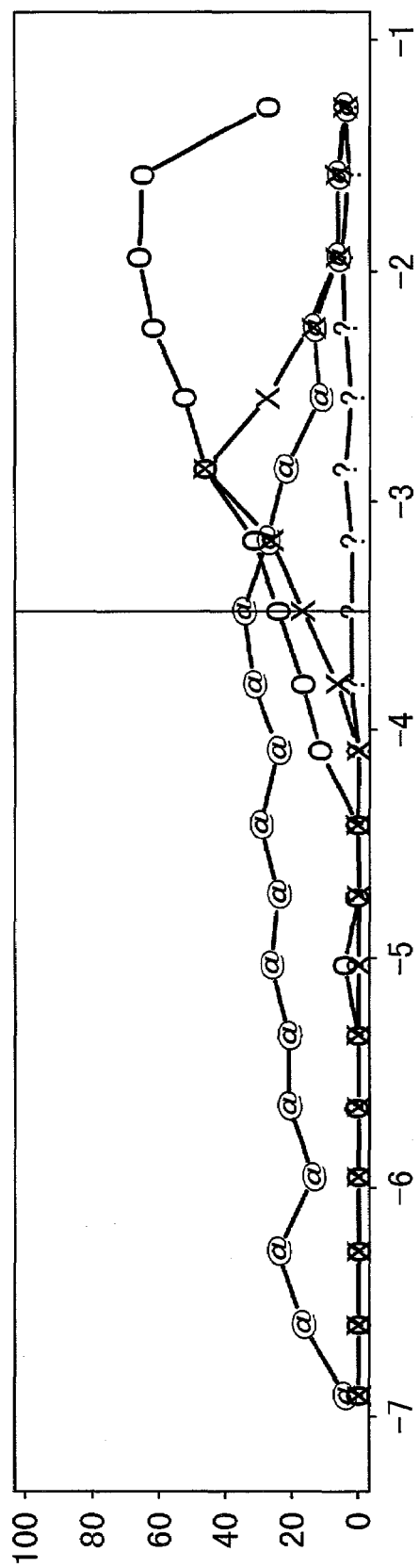
FIG. 16 is a graph of the evaluation factor shows the other angular variance.
Figure 17:
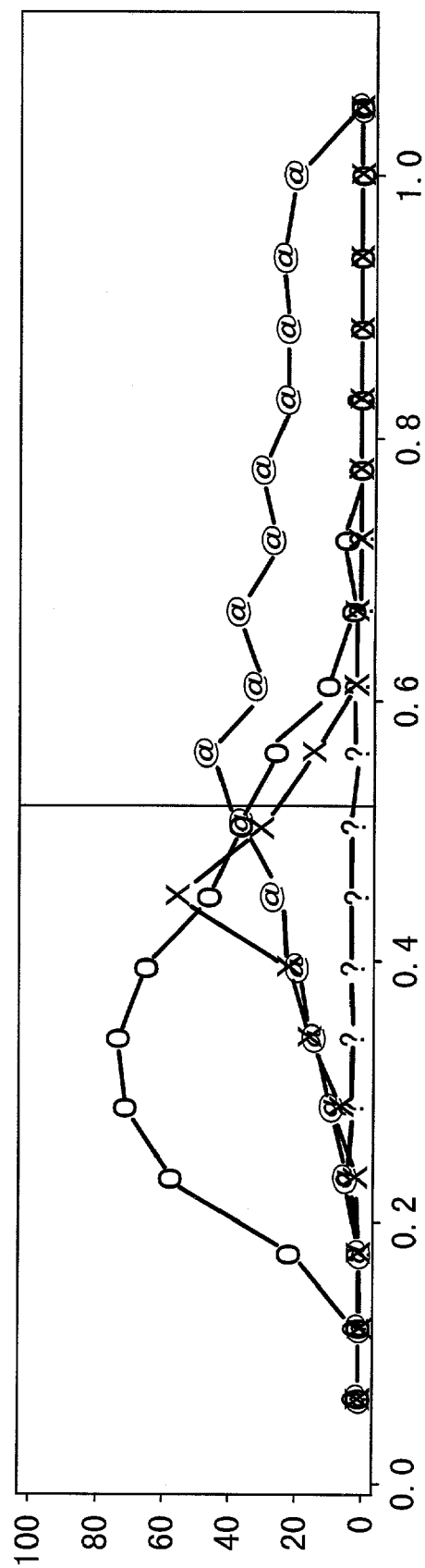
FIG. 17 is a graph of the feature quantity showing other angular variance.
Figure 18:
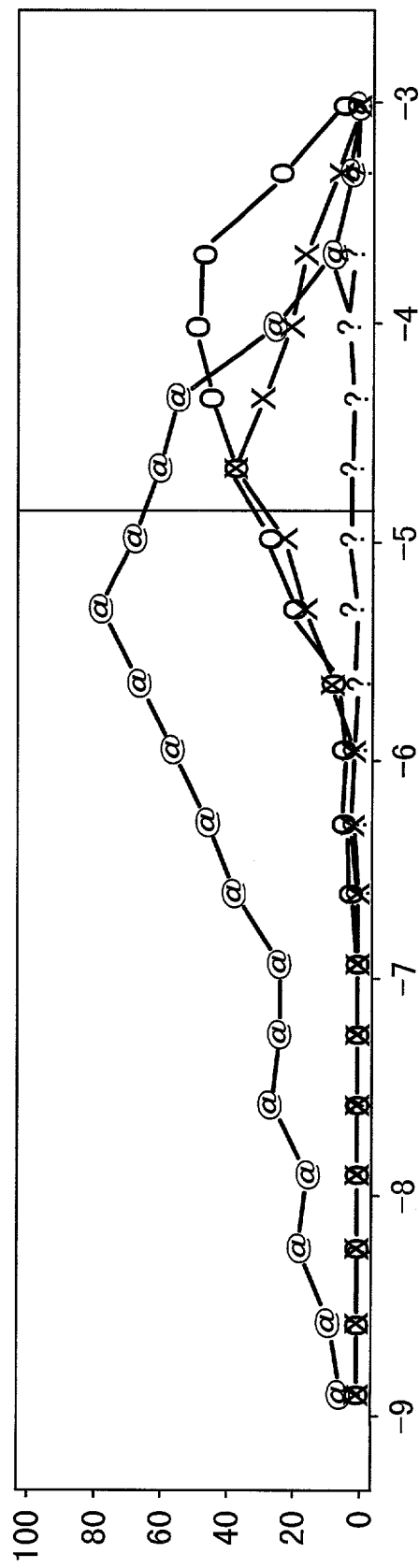
FIG. 18 is a graph of the evaluation factor showing other angular variance.
Figure 19:
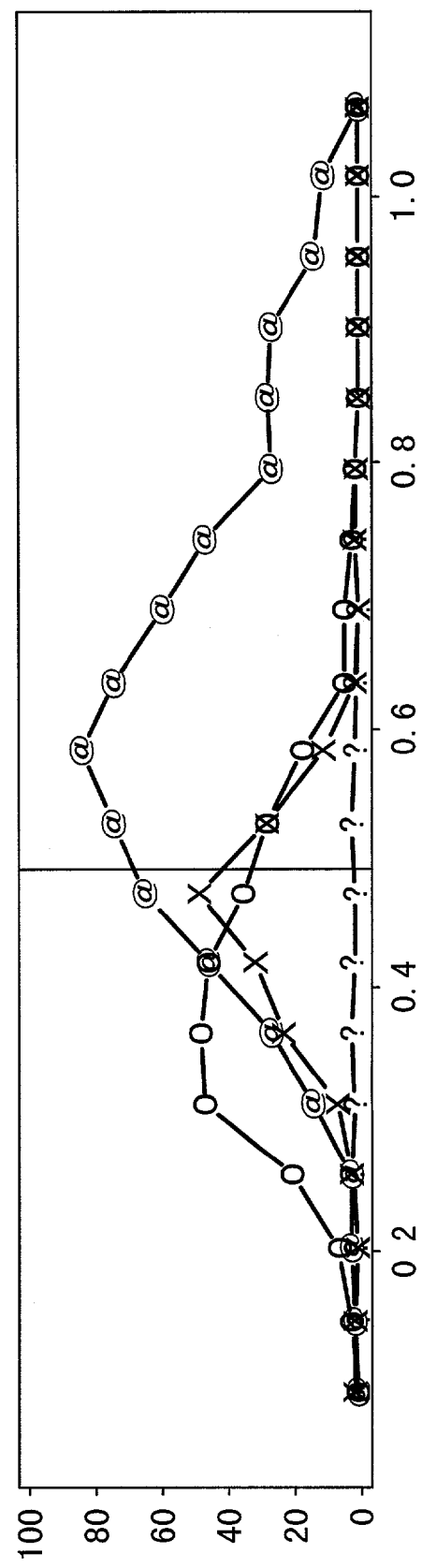
FIG. 19 is a graph of the feature quantity showing other angular variance.

Four sets of FIG. 12 and FIG. 13; FIG. 14 and FIG. 15; FIG. 16, and FIG. 17; and FIG. 18 and FIG. 19 show high correlation between the evaluation factor (the determination factor) and the filling percentage. The set of FIG. 12 and FIG. 13 shows the correlation of the coarse grain region, the set of FIG. 14 and FIG. 15 shows the correlation of the small grain region, the set of FIG. 16 and FIG. 17 shows the correlation of the gain mixture region, and the set of FIG. 18 and FIG. 19 shows the correlation of the welding region.

The horizontal axis of FIG. 12 shows the evaluation factor, the vertical axis shows the number of labels and FIG. 12 shows the spectrum of the evaluation factor. The symbol "○" shows the right label, the symbol "?" shows the error detection label, the symbol "@" shows a miss label and the symbol "X" shows a binary coding failure label. The horizontal axis of FIG. 13 shows the filling percentage as one of the feature quantity components. In FIG. 12, a cross point of the @ line and the circle line corresponds to the calculated threshold value T (=1.96). A cross point of the @ line and the circle line is a threshold value (=0.33) of the filling percentage in FIG. 13. The relation of FIG. 12 and FIG. 13 becomes turning-over (almost mirror symmetrical with respect to the threshold value). FIG. 12 and FIG. 13 show the height of the correlation between the determination factor and the filling percentage.

In FIG. 14, a cross point of the @ line and the circle line corresponds to the calculated threshold value T (=−2.38). In FIG. 15, the cross point of the @ line and the circle line becomes threshold value (=0.47) of the filling percentage. The relation of FIG. 14 and FIG. 15 becomes turning-over (almost mirror symmetrical with respect to the threshold value). FIG. 14 and FIG. 15 show the height of the correlation between the determination factor and the filling percentage. In FIG. 16, the neighborhood of the cross point of the @ line and the circle line corresponds to the calculated threshold value T (=−349). In FIG. 17, the neighborhood of the cross point of the @ line and the circle line is the threshold value (=0.53) of the filling percentage. The relation of FIG. 16 and FIG. 17 becomes turning-over (almost mirror symmetrical with respect to the threshold value). FIG. 16 and FIG. 17 show the height of the correlation between the determination factor and the filling percentage.

In FIG. 18, the neighborhood of the cross point of the @ line and the circle line corresponds to the calculated threshold value T(=−4.79). The neighborhood of the cross point of the @ line and the circle line is the threshold value (=0.48) of the filling percentage in FIG. 19. The relation of FIG. 18 and FIG. 19 becomes turning-over (almost mirror symmetrical with respect to the threshold value). FIG. 18 and FIG. 19 show the height of the correlation between the determination factor and the filling percentage.

The number of voids and the size of each of the voids are important decisively to evaluate a remaining lifetime and the material of the mechanical element is classified into a class C1 (corresponding to the void class) in which the material is in the first half of the lifetime or a class C2 (corresponding to the non-void class) in which the material is in the second half of the lifetime.

Next, an operation of the void determining unit 6 will be described below. The void determining unit 6 receives the detection labels as the test data. The void determining unit 6 calculates feature quantities of each of the detection labels to generate a feature quantity vector X (x1, x2, x3, x4, x5). At a step S9, the void determining unit 6 receives the coefficient vector I 4 from the calculating unit 3. The void determining unit 6 calculates an inner product of each of the feature quantity vector X and the coefficient vector I to produce a determination quantity F. The determination quantity F is shown as the inner product defined in the following equation.

$$F = I \cdot X$$
$$= I_1 x_1 + I_2 x_2 + I_3 x_3 + I_4 x_4 + I_5 x_5$$

At a step s10, the void determining unit 6 receives the threshold value T. The void determining unit 6 classifies the detection labels into the void class and the non-void class based on the determination quantities and the threshold value.

Thus, through a series of processes of the calculation, all labels are separated into the void class and the non-void class. The void class includes void labels normally detected as the void label and the non-void labels erroneously detected as the void labels.

The axis that the separation degree of two classes becomes high is calculated from the N (N is a positive integer, and 5 in this case) dimensional space feature quantity vector by the canonical determining method. The high separation degree of two classes is equivalent to calculation of the axis by which the ratio of the inter-class variance (the numerator of the equation (1)) and the intra-class variances (the denominator of the equation (1)) becomes the largest. An evaluation function as the determination quantity F is a mapping of the feature quantity vector to the axis. This mapping is the linear summation of N dimensional feature quantities $x_j$ (j=5 in this case) and is calculated as the above-mentioned inner product.

Next, the threshold value of the inner product I·X as the determination quantity (a evaluation factor) is calculated from the above three subset labels. The evaluation factor I·X is calculated about all the labels which are (right label+error detection label+miss label). The difference between the maximum and the minimum is divided equally in 100. The inner product I·x that the number of labels of (the error detection label+miss labels) is the smallest is determined as the threshold value of the void/non-void determination.

The void calculating unit 3 calculates the inner product I·$X_k$ (=F) about all labels at the step S9, where k is the continuous label number. The vector $X_k$ is the 5-dimension vector having five feature quantities as mentioned above. The void determining unit 6 calculates the evaluation factor about all the labels at the step S9 based on the coefficient vector I. Next, the following determination is carried out at the step S10. $F_k=I·X_k>=T$: The label $X_k$ is void. $F_k=I·X_k<T$: The label $X_k$ is non-void. Moreover, if F>=T, the size of the void is determined. The number of voids and the size of each of voids are outputted from the void determining unit 6.

Figure 6:
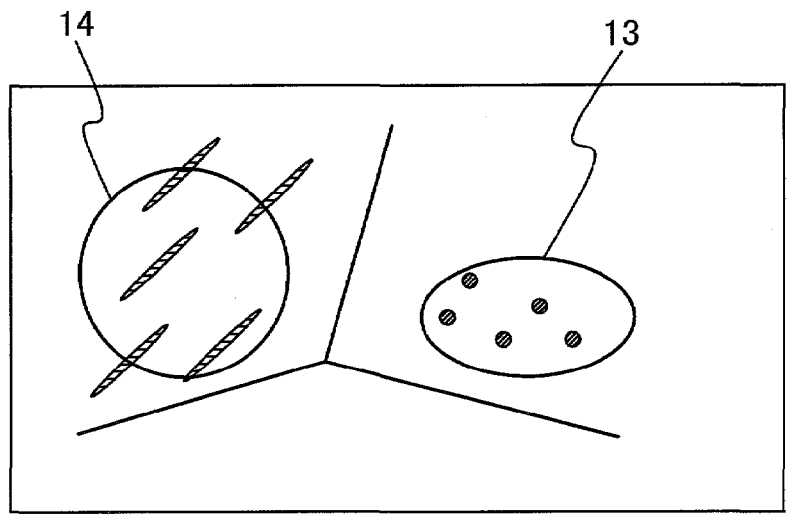
FIG. 6 is a diagram showing classification of labels.

In this way, as shown in FIG. 6, the void labels 14 can be distinguished from the non-void labels 13. At this time, because the number of voids and the size of each of voids are determined, the void determining unit 6 refers to a determination table shown in FIG. 9 based on the number of voids and the size of each of voids to determine a remaining lifetime of the material of the mechanical element.

FIG. 9 shows the determination table of creep voids in the four damage levels of $I_D$, $II_D$, $III_D$ and $IV_D$. If the degradation progresses, both of the number of creep voids and the size of the creep void increase. Based on this fact, the determination table is previously prepared.

The filling percentage is the important criterion of the determination of the degradation. The precision of the degradation diagnosis becomes higher by adopting the other four criteria and using a determination factor as the mapping in the 5-dimension space. The diagnosis depending on the computer 100% is not an inferior to the diagnosis learned from the expert. Moreover, by undergoing learning, it is strongly estimated that the high precision diagnosing becomes possible.

The lifetime evaluating system of a material of a mechanical element and the method of evaluating the lifetime of the material according to the present invention can calculate a remaining lifetime without the expert in a short time. The evaluation is equivalent to the evaluation by the expert in point of the precision. Especially, the remaining lifetime evaluation becomes possible more properly by referring to the knowledge which is learned from the expert and calculating an evaluation factor and a threshold value.

What is claimed is:

1. A lifetime evaluating system comprising:
a digitalizing unit which digitizes an original metallographic image of a mechanical element to form a digital image;
an acquiring unit which acquires a plurality of labels from said digital image, wherein each of said plurality of labels is a set of pixels with a predetermined property; and
a determining unit which classifies said plurality of labels into a class of voids and a class of non-voids based on evaluation data,
wherein a lifetime of said mechanical element is determined based on a number of labels in said void class and a size of each of said labels in said void class,
wherein said evaluation data includes a filling percentage $r_C$ defined in the following equation (1), $$r_C = N_A/N_R \qquad (1)$$

wherein $N_A$ is a number of pixels in each of said plurality of labels, and $N_R$ is a number of pixels around said label.

2. A lifetime evaluating system comprising:
a digitalizing unit which digitizes an original metallographic image of a mechanical element to form a digital image;
an acquiring unit which acquires a plurality of labels from said digital image, wherein each of said plurality of labels is a set of pixels with a predetermined property; and
a determining unit which classifies said plurality of labels into a class of voids and a class of non-voids based on evaluation data,
wherein a lifetime of said mechanical element is determined based on a number of labels in said void class and a size of each of said labels in said void class,
wherein said evaluation data includes an area percentage $r_{HAZ}$ defined by the following equation (2), $$r_{HAZ} = N_M/N_T \qquad (2)$$

where $N_M$ is a total number of pixels in said label, and $N_T$ is a total number of pixels of said digital image.

3. A lifetime evaluating system comprising:
a digitalizing unit which digitizes an original metallographic image of a mechanical element to form a digital image;
an acquiring unit which acquires a plurality of labels from said digital image, wherein each of said plurality of labels is a set of pixels with a predetermined property; and
a determining unit which classifies said plurality of labels into a class of voids and a class of non-voids based on evaluation data,
wherein a lifetime of said mechanical element is determined based on a number of labels in said void class and a size of each of said labels in said void class,
wherein said evaluation data includes a coefficient vector and a threshold value, and said determining unit generates a feature vector from each of said plurality of labels and classifies said plurality of labels into said void class and said non-void class based on said feature vectors, said coefficient vector and said threshold value,
wherein said determining unit calculates an inner product of each of said feature vectors and said coefficient vector, and classifies the inner product based on said threshold value.

4. A lifetime evaluating system comprising:
a digitalizing unit which digitizes an original metallographic image of a mechanical element to form a digital image;
an acquiring unit which acquires a plurality of labels from said digital image, wherein each of said plurality of labels is a set of pixels with a predetermined property; and
a determining unit which classifies said plurality of labels into a class of voids and a class of non-voids based on evaluation data,
wherein a lifetime of said mechanical element is determined based on a number of labels in said void class and a size of each of said labels in said void class,
wherein said evaluation data includes a coefficient vector and a threshold value, and said determining unit generates a feature vector from each of said plurality of labels and classifies said plurality of labels into said void class and said non-void class based on said feature vectors, said coefficient vector and said threshold value,
wherein said feature vector has geometrical feature quantities and optical feature quantities.

5. The lifetime evaluating system according to claim 4, wherein one of said geometrical feature quantities is a filling percentage $r_C$, and one of said optical feature quantities is a normalized brightness average, said filling percentage is shown by the following equation (3), $$r_C = N_A/N_R \quad (3)$$

wherein $N_A$ is a number of pixels in each of said plurality of labels, and $N_R$ is a number of pixels around said label, and said normalized brightness $S_A$ is shown by the following equation (4), $$S_A = (B_L - B_A)/H_A \quad (4)$$

where $B_L$ is an average brightness of one label, $B_A$ is an average brightness of a whole of said digital image, and $H_A$ is a brightness standard deviation of a whole of said digital image.

6. The lifetime evaluating system according to claim 4, wherein one of said optical feature quantities is a normalized brightness average $S_H$ defined by the following equation (5), $$S_H = H_L/H_A, \quad (5)$$

where $H_L$ is said brightness standard deviation of one label, and $H_A$ is a brightness standard deviation of a whole of said digital image.

7. The lifetime evaluating system according to claim 4, wherein one of said geometrical feature quantities is an aspect ratio $r_A$ defined by the following equation (6), $$r_A = A_L/A_S \quad (6)$$

where $A_L$ is a long axis length of one label and $A_S$ is a short axis length.

8. The lifetime evaluating system according to claim 4, wherein one of said geometrical feature quantities is an area percentage $r_{HAZ}$ defined by the following equation (7), $$r_{HAZ} = N_M/N_T \quad (7)$$

where $N_M$ is a total number of pixels in said label, and $N_T$ is a total number of pixels of said digital image.

9. The lifetime evaluating system according to claim 4, wherein in a separation θ between said void class and said non-void class, a denominator of said separation θ is a summation of an intra-variance of said void class and that of said non-void class, and a numerator of said separation θ is an inter-class variance, and said coefficient vector is calculated such that said separation θ is maximized.

10. The lifetime evaluating system according to claim 9, wherein $$\theta = (I^T d)^2 / [\{I^T(S_{C1} + S_{C2})I\}(n_{C1} + n_{C2} - 2)]$$

where $n_{C1}$ is the number of labels in said void class, $n_{C2}$ is the number of labels in said non-void class, I is a matrix of said coefficient vector, T of an upper right subscript means transposition of a matrix, $S_{C1}$ is a matrix having as one element, a summation of squares of difference of one of feature quantities of each of said feature vectors from an average corresponding to said one feature quantity in said void class, $S_{C2}$ is a matrix having as one element, a summation of squares of difference of one of feature quantities of each of said feature vectors from an average corresponding to said one feature quantity in said non-void class, and d is a matrix of difference of a feature average vector in said void class and a feature average vector in said non-void class.

11. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value;
wherein said (c) classifying step comprises the steps of:
calculating an inner product of each of said feature vectors and said coefficient vector; and
classifying the detection labels based on the inner products and said threshold value.

12. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value,
wherein one of said plurality of feature quantities is a filling percentage $r_C$ defined in the following equation (1), $$r_C = N_A/N_R \quad (1)$$

wherein $N_A$ is a number of pixels in each of said plurality of labels, and $N_R$ is a number of pixels around said label.

13. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and classifying said plurality of labels into said void class and said non-void class based on said feature vectors, said coefficient vector and said threshold value;

wherein one of said plurality of feature quantities is an area percentage $r_{HAZ}$ defined by the following equation (2), $$r_{HAZ} = N_M/N_T \tag{2}$$

where $N_M$ is a total number of pixels in said label, and $N_T$ is a total number of pixels of said digital image.

14. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value;
wherein one of said geometrical feature quantities is a filling percentage $r_C$, and one of said optical feature quantities is a normalized brightness average,
said filling percentage is shown by the following equation (3), $$r_C = N_A/N_R \tag{3}$$

wherein $N_A$ is a number of pixels in each of said plurality of labels, and $N_R$ is a number of pixels around said label, and said normalized brightness $S_A$ is shown by the following equation (4), $$S_A = (B_L - B_A)/H_A \tag{4}$$

where $B_L$ is an average brightness of one label, $B_A$ is an average brightness of a whole of said digital image, and $H_A$ is a brightness standard deviation of a whole of said digital image.

15. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value;
wherein one of said optical feature quantities is a normalized brightness average $S_H$ defined by the following equation (5), $$S_H = H_L/H_A, \tag{5}$$

where $H_L$ is said brightness standard deviation of one label, and $H_A$ is a brightness standard deviation of a whole of said digital image.

16. A lifetime evaluating method comprising the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class;
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value;
wherein one of said plurality of feature quantities is an aspect ratio $r_A$ defined by the following equation (6), $$r_A = A_L/A_S \tag{6}$$

where $A_L$ is a long axis length of one label and $A_S$ is a short axis length.

17. The lifetime evaluating method according to claim 4, wherein in a separation $\theta$ between said void class and said non-void class, a denominator of said separation $\theta$ is a summation of an intra-variance of said void class and that of said non-void class, and a numerator of said separation $\theta$ is an inter-class variance, and
said coefficient vector is calculated such that said separation $\theta$ is maximized.

18. A computer readable medium in which a program for a lifetime evaluating method is recorded, wherein said lifetime evaluating method comprises the steps of:
(a) digitalizing an original metallographic image of a mechanical element to form a digital image;
(b) acquiring a plurality of labels from said digital image, wherein each of said plurality of labels is a set of pixels with a predetermined property;
(c) classifying said plurality of labels into a class of voids and a class of non-voids based on evaluation data; and
(d) determining said lifetime of said mechanical element based on the number of labels in said void class and the size of each of said labels in said void class,
wherein said evaluation data includes a coefficient vector and a threshold value,
wherein said (c) classifying step comprises the steps of:
generating a feature vector from each of said plurality of labels, said feature vector has a plurality of feature quantities as elements; and
classifying said plurality of labels into said void class and said non-void class based on said feature vectors, said coefficient vector and said threshold value, wherein said (c) classifying step comprises the steps of:
calculating an inner product of each of said feature vectors and said coefficient vector; and
classifying the detection labels based on the inner products and said threshold value.

19. The medium according to claim 18, wherein said lifetime evaluating method further comprises the step of:
(e) calculating said evaluation data from teacher labels.

* * * * *